United States Patent
Nagamatsu et al.

(10) Patent No.: US 8,674,347 B2
(45) Date of Patent: Mar. 18, 2014

(54) ORGANIC SEMICONDUCTOR MATERIAL AND ORGANIC THIN-FILM TRANSISTOR

(75) Inventors: Shuichi Nagamatsu, Fukuoka (JP); Wataru Takashima, Fukuoka (JP); Tatsuo Okauchi, Fukuoka (JP); Tetsuji Moriguchi, Fukuoka (JP); Katsuhiro Mizoguchi, Fukuoka (JP); Keiichi Kaneto, Fukuoka (JP); Shuzi Hayase, Fukuoka (JP)

(73) Assignee: Kyushu Institute of Technology, Fukuoka (JP)

( * ) Notice: Subject to any disclaimer, the term of this patent is extended or adjusted under 35 U.S.C. 154(b) by 0 days.

(21) Appl. No.: 13/254,574

(22) PCT Filed: Mar. 4, 2010

(86) PCT No.: PCT/JP2010/053577
§ 371 (c)(1),
(2), (4) Date: Sep. 2, 2011

(87) PCT Pub. No.: WO2010/101224
PCT Pub. Date: Sep. 10, 2010

(65) Prior Publication Data
US 2012/0001162 A1 Jan. 5, 2012

(30) Foreign Application Priority Data

Mar. 6, 2009 (JP) .................. 2009-053759

(51) Int. Cl.
*H01L 29/08* (2006.01)
*H01L 51/00* (2006.01)

(52) U.S. Cl.
USPC .................... 257/40; 257/E51.006

(58) Field of Classification Search
USPC ............... 257/40, E51.006, E51.025; 438/99
See application file for complete search history.

(56) References Cited

U.S. PATENT DOCUMENTS 5,380,613 A * 1/1995 Ueda et al. ............... 430/58.35
(Continued)

FOREIGN PATENT DOCUMENTS

JP          05-100451          4/1993
(Continued)

OTHER PUBLICATIONS

Newman et al., "Introduction to organic thin film transistors and design of n-channel organic semiconductors", Chem. Mater., vol. 16, No. 23, 2004, 4436-4451.*
(Continued)

*Primary Examiner* — Steven Loke
*Assistant Examiner* — Sitaramarao S Yechuri
(74) *Attorney, Agent, or Firm* — Wenderoth, Lind & Ponack, L.L.P.

(57) ABSTRACT

An organic thin-film transistor comprising a gate electrode, a gate insulator layer, an organic semiconductor layer, a source electrode and a drain electrode wherein the organic semiconductor layer consists of the organic semiconductor material having the structure represented by the general formula (1) shown below, and the organic semiconductor layer has crystallinity:

(1)

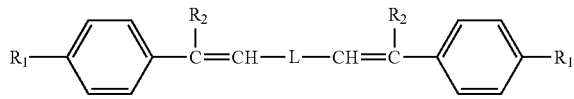

wherein L represents a bivalent linker group having the structure consisting of one group or any combination of two or more groups selected from unsubstituted or fluorinated benzene residue, unsubstituted or fluorinated thiophene residue, unsubstituted or fluorinated thienothophene residue;
$R_1$ represents carbonyl group, cyano group or $C_1$-$C_6$ fluorinated alkyl group;
$R_2$ represents halogen atom, cyano group, carbonyl group or acetyl group.

1 Claim, 6 Drawing Sheets

(56) References Cited

U.S. PATENT DOCUMENTS

| | | |
|---|---|---|
| 7,521,710 B2 | 4/2009 | Nakamura et al. |
| 2007/0187674 A1 | 8/2007 | Nakamura et al. |
| 2009/0140240 A1 | 6/2009 | Nakamura et al. |
| 2009/0159876 A1 | 6/2009 | Ohba et al. |
| 2009/0159878 A1 | 6/2009 | Nakamura et al. |
| 2010/0025670 A1 | 2/2010 | Saito et al. |

FOREIGN PATENT DOCUMENTS

| | | |
|---|---|---|
| JP | 06-059486 | 3/1994 |
| JP | 06-123986 | 5/1994 |
| JP | 2000-012330 | 1/2000 |
| JP | 2004-214482 | 7/2004 |
| JP | 2007-116115 | 5/2007 |
| WO | 2006/085005 | 8/2006 |
| WO | 2007/094361 | 8/2007 |
| WO | 2008/069060 | 6/2008 |

OTHER PUBLICATIONS

International Search Report issued Apr. 6, 2010 in International (PCT) Application No. PCT/JP2010/053577, of which the present application is the national stage.

H. Detert et al., Synthesis, Structure and Solvatochromism of the Emission of Cyano-Substituted Oligo(phenylenevinylene)s, European Journal of Organic Chemistry, vol. 15, pp. 2927-2938, 2001.

H. Ryu et al., Photo- and electroluminescent properties of cyano-substituted styryl derivatives and synthesis of CN-PPV model compounds containing an alkoxy spacer for OLEDs, Tetrahedron, vol. 62, Issue 26, pp. 6236-6247, May 18, 2006.

Supplementary European Search Report issued May 7, 2013 in the corresponding European Application No. EP 10 74 8817.

* cited by examiner

ORGANIC SEMICONDUCTOR MATERIAL AND ORGANIC THIN-FILM TRANSISTOR

CROSS-REFERENCE TO RELATED APPLICATION

The present application is based on International Application No. PCT/JP2010/053577 which was filed on Mar. 4, 2010, and claims priority under 35 U.S.C. §119 from Japanese Patent Application No. 2009-053759 which was filed on Mar. 6, 2009, the entire disclosure of which, including specification, claims, drawings and summary, is incorporated herein by reference in its entirety.

BACKGROUND OF THE INVENTION

1. Field of the Invention

The present invention relates to organic thin-film transistors having a layer of the organic semiconductor material and to method for producing the same.

2. Description of the Related Art

In recent years, organic electronic devices using carrier-conductive organic compounds have been developed actively. Such organic compounds have been applied to light emitting materials, charge injection materials and charge conductive materials for organic EL devices, and organic laser oscillators (for example, see Japanese Published Unexamined Application No. 2000-12330 and Japanese Published Unexamined Application No. 6-59486). The application of those organic compounds to organic thin-film transistor has been expected.

Thin film transistors have been widely applied to switching elements for display devices such as liquid crystal displays. Although amorphous or polycrystalline silicon has been employed to the thin-film transistor, the transistor using the organic semiconductor material has been proposed in terms of its low production cost and productivity. Several organic compounds used as the organic semiconductor material have been reported.

For example, Japanese Published Unexamined Application No. 2004-214482 discloses conjugated or non-conjugated oligomers and polymers having a stilbene structure as novel organic compounds for the organic semiconductor materials with high carrier mobility. WO2007/094361 discloses that the response rate (carrier mobility) of the organic thin-film transistor may be enhanced by using a certain organic compound having styryl group for the organic semiconductor layer.

SUMMARY OF THE INVENTION

From a practical point of view, it is essential for the organic semiconductor material used for the organic semiconductor layer of light emitting material, charge injection materials and charge conductive materials of transistors and organic EL devices or the organic laser oscillators and the like to have excellent properties in all aspects such as resistance against oxygen and water, good workability as well as excellent physical, chemical and electronic connectivity with various electrode materials in addition to high carrier conductivity as the organic semiconductor material.

However, the carrier mobility of the compounds as disclosed in Japanese Published Unexamined Application No. 2004-214482 are insufficient for the organic semiconductor layer.

On the other hand, the compounds as disclosed in WO2007/094361 exhibit n-type semiconductor properties and have high carrier (electron) mobility. However, resistance against oxygen and water of those compounds is insufficient. In addition, a highly reactive metal such as calcium must be used as a cathode because of its shallow LUMO levels, electron injection levels of those compounds. Moreover, formation of the films of conventional organic semiconductor materials using a simple process such as a coating process is difficult because of their poor solubility in organic solvents and poor affinity to various substrate materials.

Thus, the fact is that no organic semiconductor materials fulfilling both requirements of carrier (electron) mobility and stability exist so far.

Under these circumstances, the object of present invention is to provide an organic semiconductor material having excellent carrier (electron) mobility, stability, and film-forming ability using a simple production process, as well as an organic thin-film transistor in which the material is used in an organic semiconductor layer.

As a result of intensive studies to solve the aforementioned problems, the present inventors discovered that an organic thin-film transistor using an organic semiconductor material having a certain structure as an organic semiconductor layer may solve the problems to achieve the present invention.

The present invention relates to an organic thin-film transistor as follows:

First aspect of the present invention provides an organic thin-film transistor comprising a gate electrode, a gate insulator layer, an organic semiconductor layer, a source electrode and a drain electrode wherein the organic semiconductor layer containing an organic semiconductor material having the structure represented by the general formula (1) shown below, and the organic semiconductor layer has the crystallinity:

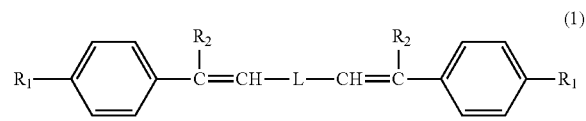

(1)

wherein L represents a bivalent linker group having the structure consisting of one group or any combination of two or more groups selected from unsubstituted or fluorinated benzene residue, unsubstituted or fluorinated thiophene residue, unsubstituted or fluorinated thienothophene residue;

$R_1$ represents carbonyl group, cyano group or $C_1$-$C_6$ fluorinated alkyl group;

$R_2$ represents halogen atom, cyano group, carbonyl group or acetyl group.

Second aspect of the present invention provides a method for manufacturing an organic thin-film transistor comprising a gate electrode, a gate insulator layer, a crystalline organic semiconductor layer, a source electrode and a drain electrode, wherein the organic semiconductor layer is formed by coating of an organic solvent containing the organic semiconductor material having the structure represented by the aforementioned general formula (1).

Third aspect of the present invention provides a method for manufacturing an organic thin-film transistor comprising a gate electrode, a gate insulator layer, a crystalline organic semiconductor layer, a source electrode and a drain electrode wherein the organic semiconductor layer is formed by vapor-deposition of the organic semiconductor material having the structure represented by the aforementioned general formula (1).

The present invention provides advantages as follows.

The organic thin-film transistor of the present invention in which the organic semiconductor material of the present invention has high carrier mobility, excellent physical, chemical and electronic connectivity with various electrode materials, and high stability to air and moisture.

Accordingly, the organic semiconductor material of the present invention has excellent properties for practical use in all aspects as an organic semiconductor layer for an organic thin-film-transistor. Thus, it is preferably applicable to the organic semiconductor layer for the organic thin-film transistor.

In addition, the organic semiconductor material of the present invention has an advantage of film-forming ability using a simple coating process because of its high solubility in conventional organic solvents.

DESCRIPTION OF THE EMBODIMENTS

Figure 1:
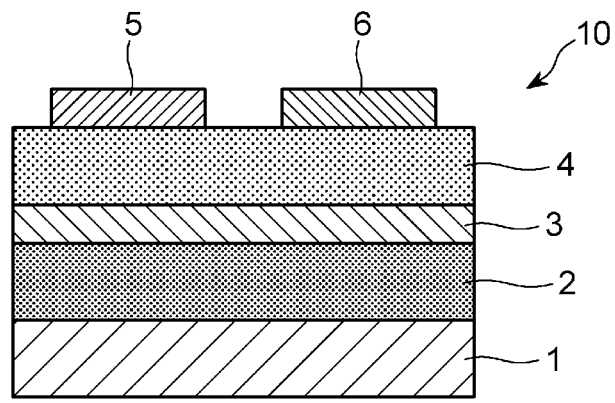
FIG. 1 shows a schematic view of one example of the organic thin-film transistor having the organic semiconductor layer consisting of the organic semiconductor material of the present invention.

Hereinafter the present invention will be explained in detail.
(Organic Semiconductor Material)

The first characteristic of the organic semiconductor material of the present invention is the structure represented by the general formula (1) shown below. Hereinafter, the compound represented by the general formula (1) may be referred to as "the compound of the present invention".

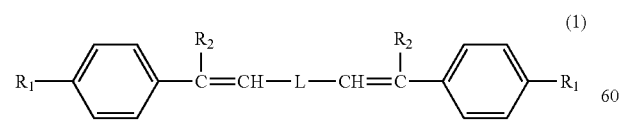

(1)

In the aforementioned general formula (1), L represents a bivalent linker group having the structure consisting of one group or any combination of two or more groups selected from unsubstituted or substituted vinylene group, acetylene group, unsubstituted or substituted aromatic hydrocarbon residue, unsubstituted or substituted fused aromatic hydrocarbon residue, unsubstituted or substituted heteroaromatic residue, unsubstituted or substituted fused heteroaromatic residue.

The aforementioned aromatic hydrocarbon residue includes benzene residue.

The fused aromatic hydrocarbon residue includes naphthalene residue, phenanthrene residue, anthracene residue, perylene residue, pyrene residue, chrysene residue, pentacene residue, phenazine residue, tetracene residue, triphenylene residue, picene residue and the like.

The heteroaromatic residue includes thiophene residue, furan residue, pyrrole residue, pyrazole residue, imidazole residue, triazole residue, oxazole residue, thiazole residue, thiadiazole residue, pyridine residue, pyrimidine residue, triazine residue, pyradine residue and the like.

The fused heteroaromatic residue includes fluorene residue, indole residue, carbazole residue, benzothiophene residue, benzofuran residue, thienothiophene residue, thiazolothiazole residue, dibenzothiophene residue, dibenzofuran residue, dithienothiophene residue, benzoimidazole residue, benzooxazole residue, purine residue, benzothiophenebenzothiophene residue, dibenzobenzodifuran residue, acrydine residue, quinoline residue and the like.

The preferable example of the L includes the group having the structure consisting of one group or any combination of two or more groups selected from unsubstituted or substituted vinylene group, unsubstituted or substituted benzene residue, unsubstituted or substituted naphthalene residue, unsubstituted or substituted anthracene residue, unsubstituted or substituted perylene residue, unsubstituted or substituted pyrene residue, unsubstituted or substituted thiophene residue, unsubstituted or substituted furan residue, unsubstituted or substituted pyrrole residue, unsubstituted or substituted thiazole residue, unsubstituted or substituted benzothiophene residue, unsubstituted or substituted benzofuran residue, unsubstituted or substituted thienothiophene residue.

From the standpoint of sufficient electron-withdrawing effect of electron-withdrawing portion of R1 and R2 to L, the main molecular skeleton, L has the structure preferably consisting of four or less groups selected from the aforementioned groups, more preferably consisting of two or less groups selected from the aforementioned groups.

In addition, the more preferable example of the L includes unsubstituted benzene residue represented by formula (2) shown below, unsubstituted thiophene residue represented by formula (3) shown below, unsubstituted thienothiophene residue represented by formula (4) shown below, unsubstituted furan residue represented by formula (5) shown below, and unsubstituted pyrrole residue represented by formula (6) shown below, in which unsubstituted benzene residue, unsubstituted thiophene residue and unsubstituted thienothiophene residue are particularly preferred.

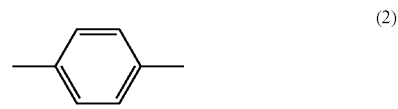

(2)

(3)

-continued

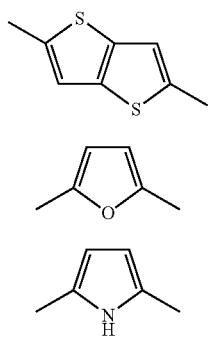

In the aforementioned general formula (1), $R_1$ represents carbonyl group, cyano group or $C_1$-$C_{12}$ fluorinated alkyl group.

Here, fluorinated alkyl group is particularly preferred. When $R_1$ is fluorinated alkyl group, orderliness is brought to the compound because of not only electron-withdrawing property of fluorine atom but also interaction between the fluorinated alkyl groups. As a result, the compound of the present invention tends to become more crystalline.

The carbon number of the fluorinated alkyl group of the compound of the present invention is 1 to 12, preferably 1 to 6, particularly preferably 1 to 3. When the carbon number of the fluorinated alkyl group is 1 to 6, significant loss of film-forming property upon film formation due to the excess of the carbon atom may be avoided. Moreover, when the carbon number of the fluorinated alkyl group is 1 to 3, no significant change of molecular orientation upon film formation due to the excess of the carbon atom takes place. As a result, electron mobility and ON/OFF ratio of the organic thin-film transistor are not significantly affected.

Furthermore, a characteristic of the compound of the present invention is that $R_1$ is located on para position of benzene ring, which tends to enhance the carrier mobility of the compound of the present invention.

$R_2$ represents electron withdrawing halogen atom, cyano group or acetyl group. Above all, cyano group is particularly preferred in the compound of the present invention represented by the general formula (1) since it contributes to crystallinity of the compound to enhance the intermolecular interaction without undue steric hindrance.

Some particular examples of the compound of the present invention will be shown below. However, they are shown just for illustrative purposes and they do not limit the scope of the compound of the present invention.

Compounds (A1)-(A4) may be exemplified as examples in which L consists of aromatic hydrocarbon residue.

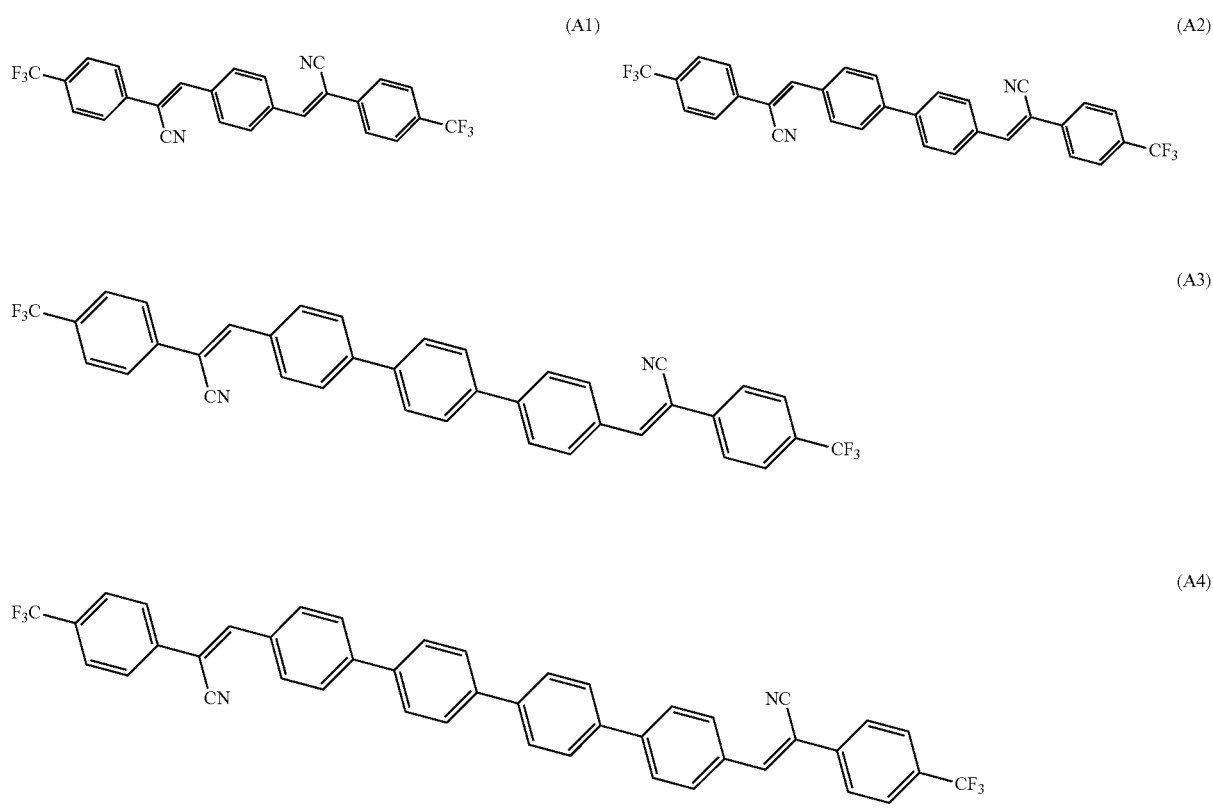 [SMILES: N#C/C(=C\c1ccc(/C=C(\C#N)c2ccc(C(F)(F)F)cc2)cc1)c1ccc(C(F)(F)F)cc1 ; N#C/C(=C\c1ccc(-c2ccc(/C=C(\C#N)c3ccc(C(F)(F)F)cc3)cc2)cc1)c1ccc(C(F)(F)F)cc1 ; N#C/C(=C\c1ccc(-c2ccc(-c3ccc(/C=C(\C#N)c4ccc(C(F)(F)F)cc4)cc3)cc2)cc1)c1ccc(C(F)(F)F)cc1 ; N#C/C(=C\c1ccc(-c2ccc(-c3ccc(-c4ccc(/C=C(\C#N)c5ccc(C(F)(F)F)cc5)cc4)cc3)cc2)cc1)c1ccc(C(F)(F)F)cc1]

Compounds (B1)-(B6) may be exemplified as examples in which L consists of fused aromatic hydrocarbon residue.
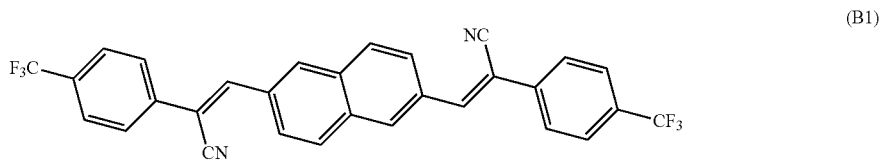
(B1)
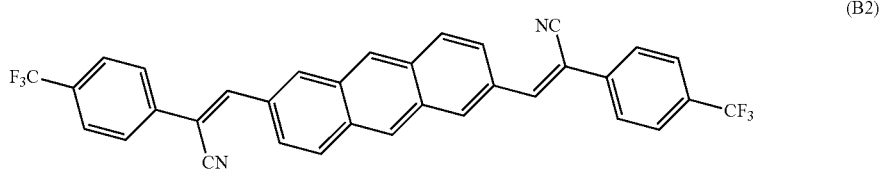
(B2)
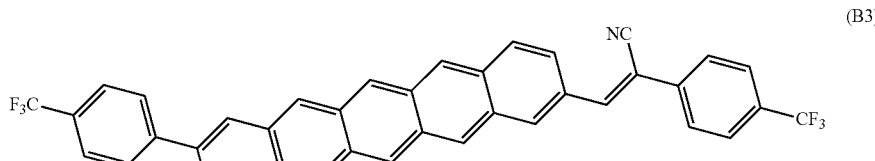
(B3)
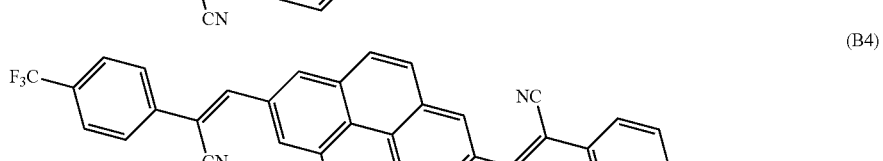
(B4)
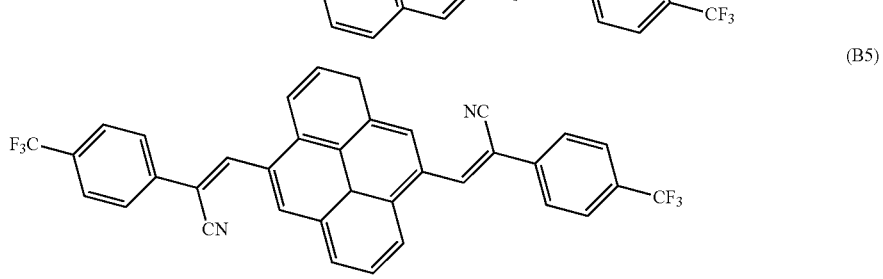
(B5)
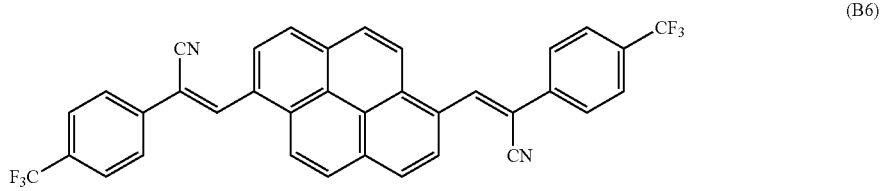
(B6)
Compounds (C1)-(C7) may be exemplified as examples in which L consists of heteroaromatic residue.
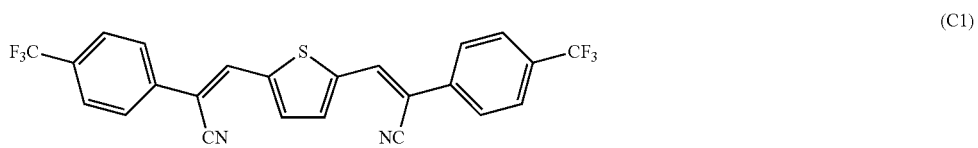
(C1)
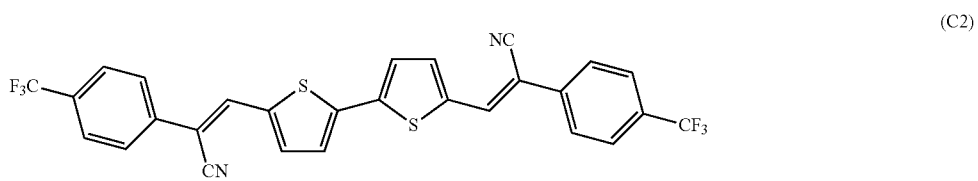
(C2)

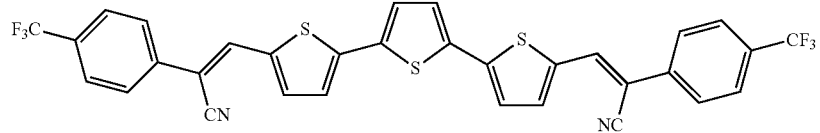
(C3)
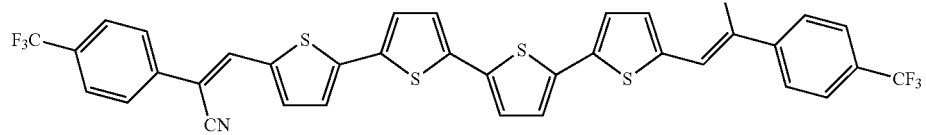
(C4)
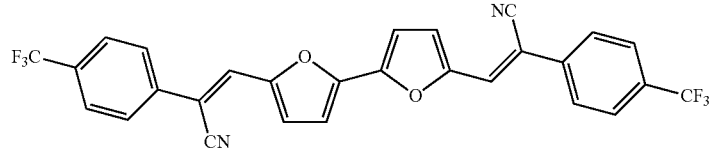
(C5)
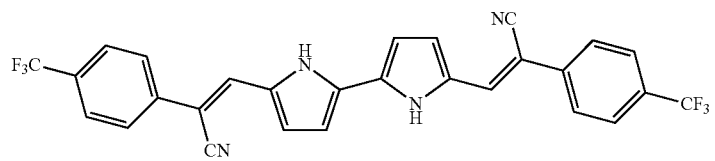
(C6)
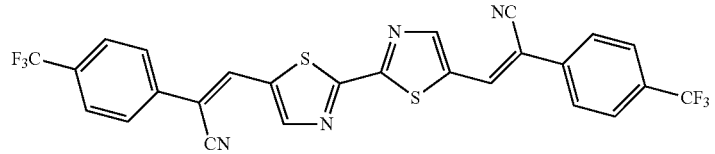
(C7)
Compounds (D1)-(D6) may be exemplified as examples in which L consists of aromatic fused heterocyclic hydrocarbon residue.
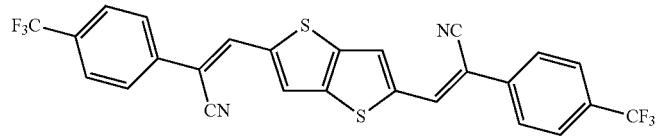
(D1)
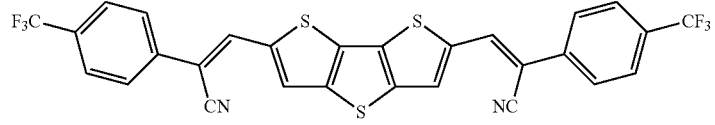
(D2)
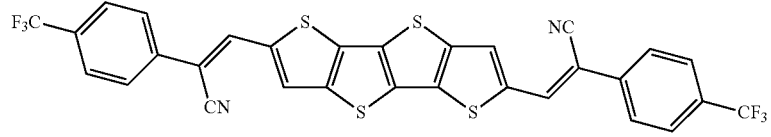
(D3)
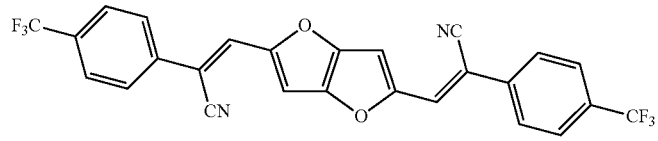
(D4)

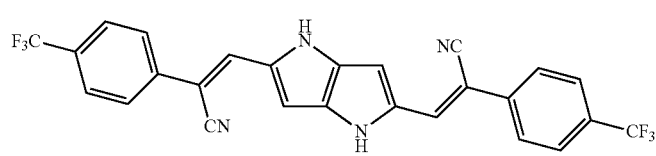
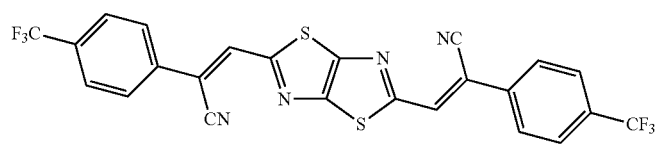

Compounds (E1)-(E7) may be exemplified as examples in which L consists of substituted aromatic hydrocarbon residue.

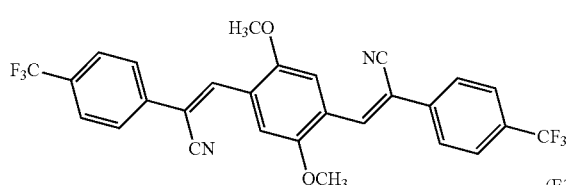
(E1)

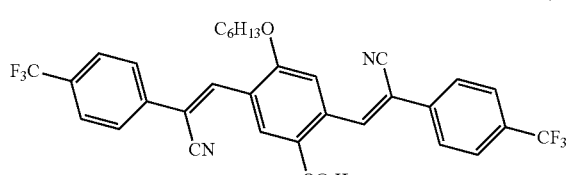
(E2)

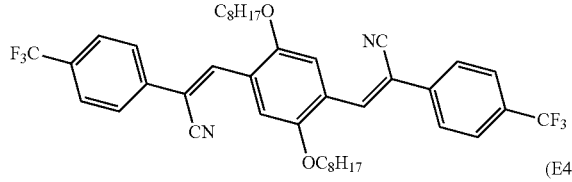
(E3)

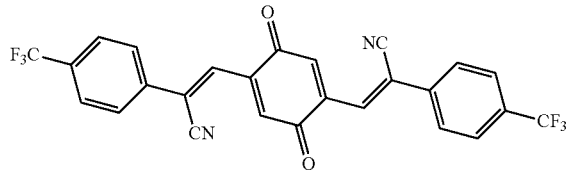
(E4)

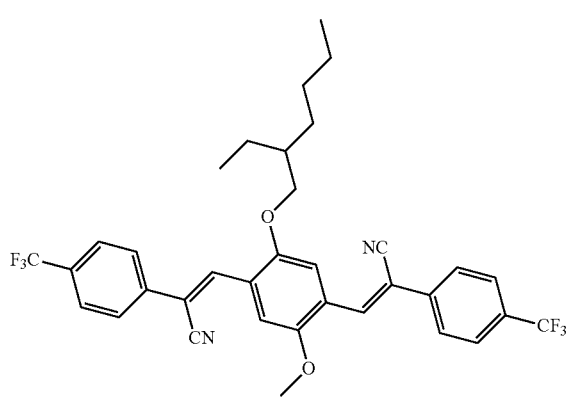
(E5)

(D5)

(D6)

-continued

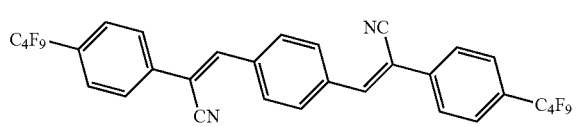
(E6)

(E7)

Compounds (F1)-(F4) may be exemplified as examples in which $R_1$ is halogenated alkyl group.

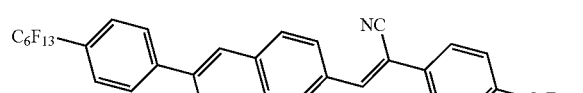
(F1)

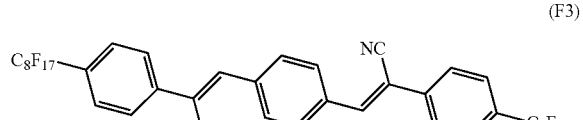
(F2)

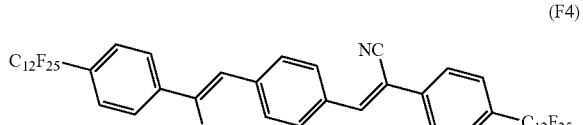
(F3)

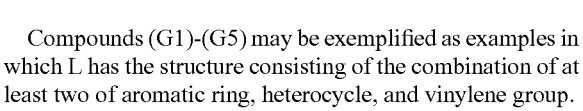
(F4)

Compounds (G1)-(G5) may be exemplified as examples in which L has the structure consisting of the combination of at least two of aromatic ring, heterocycle, and vinylene group.

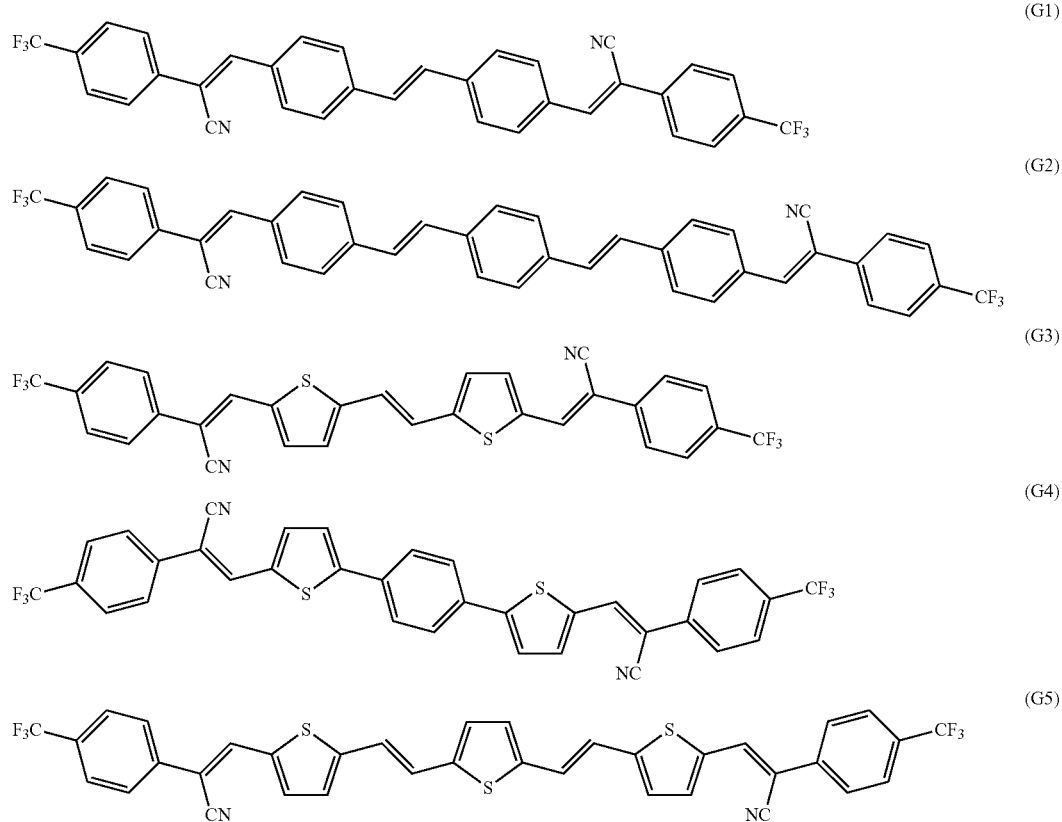
Compounds (H1)-(H7) may be exemplified as examples in which L particularly has the structure consisting of the combination of fused aromatic ring and fused heterocycle among the examples in which L consists of fused heteroaromatic group.
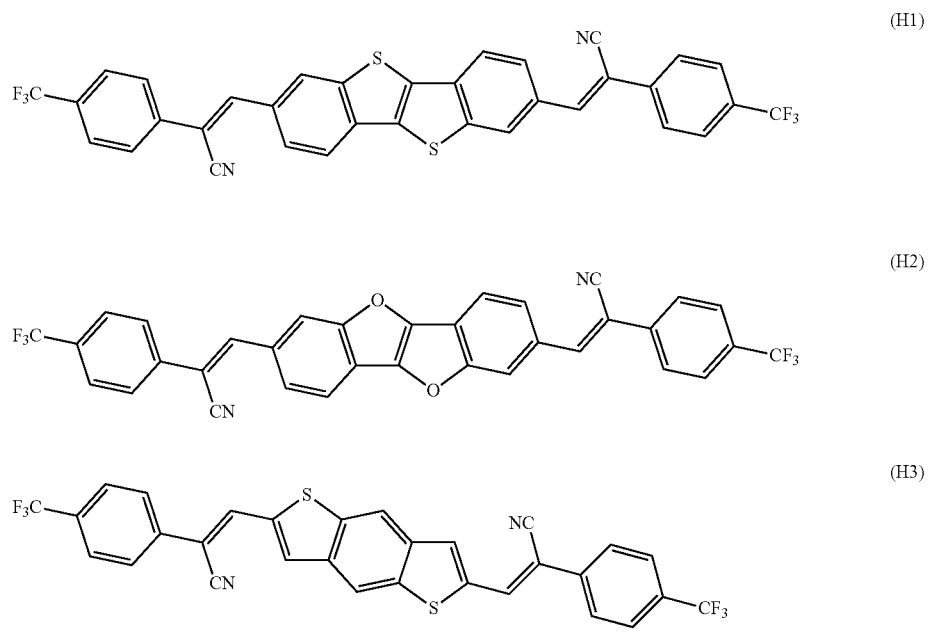

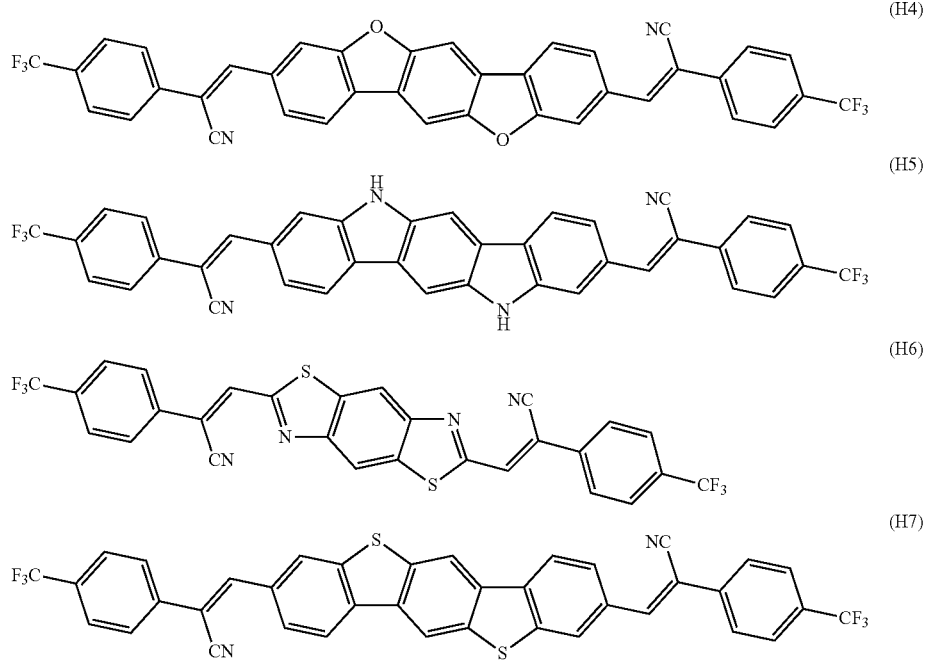

Compounds (I1)-(I3) may be exemplified as other examples.

Among the compounds of the present invention, the compound having crystallinity is particularly preferred. When the compound of the present invention has crystallinity, a short intermolecular distance facilitates electron transfer. Also, it has the advantage of stable electronic property because of a constant intermolecular distance. In the present invention, the terms "crystalline" and "have crystallinity" mean that second or higher order reflection may be substantially observed in X-ray diffraction (XRD) measurement.

As described below, the compound of the present invention may be preferably applied to the organic semiconductor layer in the form of thin-film having the thickness of about 1 μm or less. Accordingly, it is desirable that the compound of the present invention has crystallinity not only in bulk form but also in the form of a thin-film organic semiconductor layer.

Moreover, the compound of the present invention preferably has a symmetry and it is particularly preferable that it has a point symmetry center.

Among the compounds as exemplified above, the compounds with a plane symmetry include the compounds (C1), (C3), (D2) and (H5). The compounds with a point symmetry include the compounds (A1)-(A4), (B1)-(B6), (C2), (C4)-(C7), (D1), (D3)-(D6), (E1)-(E4), (E6), (E7), (F1)-(F4), (G1)-(G4), (H1)-(H7), and (I1)-(I3).

The aforementioned compounds of the present invention have a high carrier mobility, which is 0.01[cm$^2$/V·sec] or more even without removing oxygen and moisture. Also, the compound of the present invention is highly stable against air (oxygen) and moisture and hard to be oxidized.

The compound of the present invention is soluble in conventional organic solvents as described below. Accordingly, the thin film of the compound of the present invention may be formed by means of coating method such as cast coating, spin coating, screen printing, and inkjet printing using the solution prepared by dissolving the compound of the present invention in appropriate solvent and optionally adding additive.

The solvent is not particularly limited so far as it may dissolve the compound of the present invention to an appropriate concentration. The example of the solvent includes haloalkane solvents such as chloroform and 1,2-dichloroethane; aromatic solvents such as toluene, o-dichlorobenzene, nitrobenzene and m-cresol; N-methylpyrrolidone and carbon disulfide.

One compound or any combination of two or more compounds selected from the compounds of the present invention may be employed. Also, more than one mixed thin films or laminated films may be formed by using organic semiconductor material known in the art such as pentacene, thiophene oligomer and fullerene together with the compound of the present invention.

The compound of the present invention may be synthesized by means of any methods known in the art of organic synthesis. Particular methods include bromination, cyanizaiton and aldehyde formation. Knoevenagel condensation reaction is preferably carried out as the final step of the synthesis since the yield of 70% or more may be achieved.

(Organic Thin-Film Transistor)

As mentioned above, the compounds of the present invention are soluble in conventional organic solvents as well as they have stability against air and moisture. Accordingly, the organic semiconductor layer for organic thin-film transistors having superior properties and high reliability may be formed with coating process by using simple device, although it may also be formed on substrate by vacuum sputtering process.

FIG. 1 shows a schematic cross sectional view of one of the organic thin-film transistors having the organic semiconductor layer consisting of the organic semiconductor material of the present invention.

Figure 2:
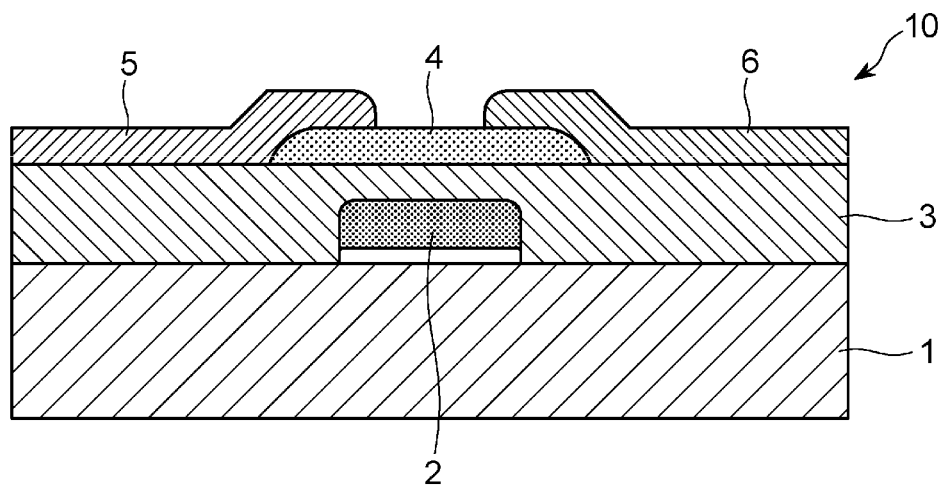
FIG. 2 shows a schematic view of another example of the organic thin-film transistor having the organic semiconductor layer consisting of the organic semiconductor material of the present invention.

The organic thin-film transistor 10 (hereinafter, it may be abbreviated to "transistor 10"), has the structure in which a gate electrode 2, a gate insulator layer 3, and an organic semiconductor layer 4 are laminated on a substrate 1 in that order, and a pair of a source electrode 5 and a drain electrode 6 are formed on the organic semiconductor layer 4. The structure shown here is one embodiment of the organic thin-film transistor using the organic semiconductor material of the present invention. The organic semiconductor material of the present invention may be applicable nOt only to the organic thin-film transistor as shown in FIG. 1, but also to any organic thin-film transistors including the one as shown in FIG. 2.

The substrate 1 is for ensuring the self-supporting property of the transistor 10. The material used for the substrate 1 is not particularly limited and various substrates such as the one made of glass, resins and semiconductor materials such as Si may be preferably employed. The Si substrate is preferably employed from the viewpoint of workability and the mechanical strength of the substrate. In the field of electronic paper and the like, highly flexible resins such as polyethylene naphthalate (PEN) may be preferably employed as the substrate 1. Furthermore, in the present embodiment, the substrate 1 and the gate electrode 2 are formed by using different materials, however, from the viewpoint of the self-supporting property of the transistor 10, the gate electrode 2 having the thickness sufficient to be a self-supporting film (self-supporting layer) may be employed so that it may act as the substrate 1 as well.

The gate electrode 2 is used for controlling the source-drain current. The material used for the gate electrode 2 is not particularly limited as long as it is conductive. For example, metals such as chromium (Cr), tantalum (Ta), titanium (Ti), copper (Cu), aluminum (Al), molybdenum (Mo), tungsten (W), nickel (Ni), gold (Au), palladium (Pd), platinum (Pt), silver (Ag), tin (Sn), lithium (Li) and calcium (Ca); oxides of these metals; indium tin oxide (ITO) and zinc oxide (ZnO); conductive polymers known in the art such as conductive polyaniline, conductive polypyrrole and conductive polythiazyl may preferably be used as the material for the gate electrode 2.

In case that the substrate 1 is employed, the thickness of the gate electrode 2 is not particularly limited, which is typically from 10 nm to 150 mm.

On the other hand, if the gate electrode 2 also serves as the substrate, the thickness of the gate electrode 2 is preferably from 10 μm to 0.5 mm to ensure sufficient self-supporting property.

The gate insulator layer 3 is formed between the gate electrode 2 and the organic semiconductor layer 4. The material used for the gate insulator layer 3 is not limited so far as it has the aforementioned function. In particular, the gate insulator layer 3 may be the insulator layer consisting of at least one of metal oxide film such as silicon oxide ($SiO_2$), aluminum oxide ($Al_2O_3$) and tantulum oxide ($Ta_2O_5$); organic compound such as polyvinylphenol, polyimide, polyvinyl alcohol, polyethylene, polyethyleneterephthalate, polyvinylidene fluoride, polymethylmethacrylate, polycarbonate, polyethylene fluoride, polystyrene, polyxylylene, cellulose, pullulan and Cytop™. Especially, when Si substrate which is preferred when the gate electrode 2 also serves as the substrate is used as the gate electrode 2, $SiO_2$ formed by oxidizing its surface may be used as the gate insulator layer 3.

The thickness of the gate insulator layer 3 is not particularly limited so far as electronic insulation between the gate electrode 2 and the source electrode 5, which is typically from 100 to 1000 nm.

The organic semiconductor layer 4 consists of the organic semiconductor material of the present invention. For forming the organic semiconductor layer 4 on the gate insulator layer 3, any film formation (deposition) processes known in the art may employed without limitation. The example of the process includes the process in which the organic semiconductor layer 4 is formed by coating the solution prepared by dissolving the compound of the present invention in appropriate solvent by means of the coating method known in the art such as cast coating, spin coating, screen printing, inkjet printing and ablation (hereinafter, abbreviated to "coating process"); and gas phase film formation process such as vacuum deposition.

As mentioned above, the advantage of the coating process is that cost-reduction and mass-production may be easily achieved since it may be carried out by simple facilities. In the coating process, the solvent is not particularly limited so far as it may dissolve the compound of the present invention to an appropriate concentration. The example of the solvent includes haloalkyl solvents such as chloroform and 1,2-dichloroethane; aromatic solvents such as toluene, o-dichlorobenzene, nitrobenzene and m-cresol; N-methylpyrrolidone and carbon disulfide.

Most of the compounds of the present invention are soluble in general organic solvents. For example, $CF_3CN$-DSB may be favorably coated by dissolving in chloroform or toluene.

Although the cost required for the gas-phase deposition process may be higher than that for the coating process, the compound of the present invention contained in the organic semiconductor layer 4 tends to be more crystalline. Accordingly, the transistor of higher performance may be fabricated. Among the gas-phase deposition processes, the vacuum deposition process is particularly preferable from the viewpoint of the film quality.

The thickness of the organic semiconductor layer 4 is not particularly limited. However, the performance of the transistor obtained strongly depend on the thickness of the active layer consisting of the organic semiconductor. The thickness of the organic semiconductor layer 4 depends on the organic semiconductor, which is generally 1 μm or less, particularly preferably from 10 to 300 nm.

The source electrode 5 and the drain electrode 6 are a pair of electrodes formed on the organic semiconductor layer 4. Current may be supplied from the source electrode 5 to the drain electrode 6 via the organic semiconductor layer 4. The material used for the source electrode 5 and the drain electrode 6 is not particularly limited so far as it is conductive, which includes the materials similar to those used for the aforementioned gate electrode 2. Among those materials, the material having small resistance on the surface in contact with the organic semiconductor layer 4 is preferred. The example of such material includes Cu, Ag, Pt, Au and Au, which is chemically stable and catalytically inert is particularly preferred.

The example of the process for forming such electrodes includes the process in which the electrode formation is carried out by vacuum deposition or sputtering of the aforementioned material through a shadow mask located on the organic semiconductor layer; the process in which the thin-film of the aforementioned material formed by vacuum deposition or sputtering is shaped by photolithographic method or lift-off method known in the art; thermal transfer of metal foil; and etching the thin-film of the aforementioned material using resist formed by inkjet printing and the like. In addition, the examples of the process also include the process in which the electrode formation is carried out by coating a solution or a dispersion of conductive polymer, or a dispersion of conductive microparticulate by direct inkjet printing on a certain pattern; the process in which electrode formation is carried out by lithography and laser ablation of the coated film of the aforementioned material; and the like.

EXAMPLES

The present invention will be illustrated by examples in more detail. However, the scope of the present invention is not intended to be limited by the examples as described below.

The reagents used are as follows:
Reagents
4-Trifluoromethylphenylacetonitrile (Tokyo Chemical Industry Co., Ltd.)
4-Methylphenylacetonitrile (Tokyo Chemical Industry Co., Ltd.)
Terephthalaldehyde (Tokyo Chemical Industry Co., Ltd.)
2,5'-Bithiophenedialdehyde (synthesized from 2,5-dibromothiophene, butyl lithium and dimethyl formamide)
2,6-Thienothiophenedialdehyde (synthesized from 2,6-dibromothienothiophene, butyl lithium and dimethyl formamide)
Biphenyl-2,2'-dicarboxamide (Tokyo Chemical Industry Co., Ltd.)
2,5-Thiophenedialdehyde (synthesized from 2,5-dibromothiophene, butyl lithium and dimethyl formamide)
4-Fluorophenylacetonitrile (Tokyo Chemical Industry Co., Ltd.)
Sodium ethoxide (Wako Pure Chemical Industries Ltd.)
Potassium t-butoxide (Wako Pure Chemical Industries Ltd.)
4-Perfluorohexylphenylacetonitrile (synthesized from iodotoluene and perfluorohexyl iodide)
2,5-Difluoroterephthalaldehyde (synthesized from difluorodibromobenzene)

Example 1

(1) Synthesis of Organic Semiconductor Material 1

Using a 50 mL round bottomed flask, 740 mg of 4-trifluoromethylphenylacetonitrile (2 mmol) and 268 mg of terephthalaldehyde (1 mmol) were dissolved in 5 mL of ethanol and 15 mL of DMF with stirring under nitrogen atmosphere. To the solution, an ethanol solution (1 mL) of 14 mg of sodium ethoxide (0.2 mmol) was added dropwise at room temperature under magnetic stirring. After the mixture was stirred for an additional 2 hours, methanol was added, and the resulting crystal was collected by suction filtration. The crystal was thoroughly washed with methanol and dried under reduced pressure in a desiccator to give a crude product. The crude product was recrystallized from chloroform to give the organic semiconductor material 1:

(2Z,2'Z)-3,3'-(1,4-phenylene)bis(2-(4-trifluoromethyl) phenylacrylonitrile) (abbrev.: $CF_3CN$-DSB, compound (A1), yellow crystal). Yield: 775 mg (80%).

(2) Fabrication of Organic Thin-Film Transistor 1

A silicon wafer with 300 nm of thermally oxidized silicon dioxide film (SUMCO CORPORATION, 1×1 cm (area: 1 $cm^2$), thickness: 525 µm) was used as a gate electrode and a gate insulator layer. A organic semiconductor layer was formed by vacuum deposition (deposition conditions were as follows. pressure: ca. $4.0 \times 10^{-6}$ ton, deposition rate: 0.5 nm/min, substrate temperature: room temperature (ca. 25° C.)) of the organic semiconductor material 1 under the condition which afforded the film thickness of ca. 50 nm on top of the silicon dioxide film.

A source electrode and a drain electrode of Au having the thickness of ca. 30 nm was formed by vacuum deposition using shadow masks, by which an organic thin film transistor 1 according to Example 1 having the structure as shown in FIG. 1 was fabricated. Channel length (L) and channel width (W) of the source and the drain electrodes are 20 µm and 2 mm, respectively.

Example 2

(1) Synthesis of Organic Semiconductor Material 2

Using a 100 mL round bottomed flask, 152.2 mg of 2,5'-bithiophenedialdehyde (0.5 mmol) and 185.2 mg of 4-trifluoromethylphenylacetonitrile (1.0 mmol) were dissolved in 7.0 mL of ethanol and 48.0 mL of DMF with stirring under nitrogen atmosphere. To the solution, an ethanol solution (1.0 mL) of 3.4 mg of sodium ethoxide (0.05 mmol) was added dropwise at room temperature under magnetic stirring. After the mixture was stirred for an additional 1 hour and cooled to 0° C., methanol was added, and the resulting crystal was collected by suction filtration. The crystal was thoroughly washed with methanol and dried under reduced pressure in a desiccator to give a crude product. The crude product was recrystallized from chloroform to give the organic semiconductor material 2:

(2Z,2'Z)-3,3'-(5,5'-bithiophene)bis(2-(4-trifluoromethyl) phenylacrylonitrile) (abbrev.: $CF_3CN$-DS2T, compound (C2), red crystal). Yield: 261.9 mg (82%).

(2) Fabrication of Organic Thin-Film Transistor 2

An organic thin-film transistor 2 according to Example 2 having the structure as shown in FIG. 1 was obtained according to the procedure similar to that of Example 1 except that the organic semiconductor material 2 was used instead of the organic semiconductor material 1.

Example 3

(1) Synthesis of Organic Semiconductor Material 3

Using a 100 mL round bottomed flask, 98.1 mg of 2,6-thienothiophenedialdehyde (0.5 mmol) and 185.2 mg of 4-trifluoromethylphenylacetonitrile (1.0 mmol) were dissolved in 5.0 mL of ethanol and 30.0 mL of DMF with stirring under nitrogen atmosphere. To the solution, an ethanol solution (1.0 mL) of 3.4 mg of sodium ethoxide (0.05 mmol) was added dropwise at room temperature under magnetic stirring. After the mixture was stirred for an additional 1 hour and cooled to 0° C., methanol was added, and the resulting crystal was collected by suction filtration. The crystal was thoroughly washed with methanol and dried under reduced pressure in a desiccator to give a crude product. The crude product was recrystallized from chloroform to give the organic semiconductor material 3:

(2Z,2'Z)-3,3'-(2,5-thieno[3,2-b]thiophene)bis(2-(4-trifluoromethyl)phenylacrylonitrile) (abbrev.: $CF_3CN$-DSTT, compound (D1), orange crystal). Yield: 225.5 mg (85%); MS (FAB$^+$) m/z=530(M$^+$).

(2) Fabrication of Organic Thin-Film Transistor 3

An organic thin film transistor 3 according to Example 3 having the structure as shown in FIG. 1 was obtained according to the procedure similar to that of Example 1 except that the organic semiconductor material 3 was used instead of the organic semiconductor material 1.

Example 4

(1) Synthesis of Organic Semiconductor Material 4

Using a 30 mL round bottomed flask, 67.1 mg of terephthalaldehyde (0.5 mmol) and 435.2 mg of acetonitrile derivative (1.0 mmol) were dissolved in ethanol (11 mL) with stirring under nitrogen atmosphere. To the solution, an ethanol solution (1.0 mL) of 3.4 mg of sodium ethoxide (0.05 mmol) was added dropwise at room temperature under magnetic stirring. After the mixture was stirred for an additional 1 hour and cooled to 0° C., methanol was added, and the resulting crystal was collected by suction filtration. The crystal was thoroughly washed with methanol and dried under reduced pressure in a desiccator to give a crude product. The crude product was recrystallized from chloroform to give the organic semiconductor material 4:

(2Z,2'Z)-3,3'-(1,4-phenylene)bis(2-(4-perfluorohexyl)phenylacrylonitrile) (abbrev.: $C_6F_{13}CN$-DSB, compound (F2)). Yield: 328.3 mg (70%).

(2) Fabrication of Organic Thin-Film Transistor 4

An organic thin film transistor 4 according to Example 4 having the structure as shown in FIG. 1 was obtained according to the procedure similar to that of Example 1 except that the organic semiconductor material 4 was used instead of the organic semiconductor material 1.

Example 5

(1) Synthesis of Organic Semiconductor Material 5

Using a 30 mL round bottomed flask, 70.1 mg of 2,5-thiophenedialdehyde (0.5 mmol) and 185.2 mg of 4-trifluoromethylphenylacetonitrile (1.0 mmol) were dissolved in 1.0 mL of ethanol and 4.0 mL of DMF with stirring under nitrogen atmosphere. To the solution, an ethanol solution (1.0 mL) of 3.4 mg of sodium ethoxide (0.05 mmol) was added dropwise at room temperature under magnetic stirring. After the mixture was stirred for an additional 1 hour, water was added followed by the addition of saturated aqueous sodium chloride. The mixture was extracted with chloroform (3 times). After drying, the solvent was evaporated. The crude product was recrystallized from hexane-chloroform to give (2Z,2'Z)-3,3'-(2,5-thiophene)bis(2-(4-trifluoromethyl)phenylacrylonitrile) (abbrev.: $CF_3CN$-DS1T, compound (C1), orange crystal). Yield: 217.0 mg (91%).

(2) Fabrication of Organic Thin-Film Transistor 5

An organic thin film transistor 5 according to Example 5 having the structure as shown in FIG. 1 was obtained according to the procedure similar to that of Example 1 except that the organic semiconductor material 5 was used instead of the organic semiconductor material 1.

Example 6

(1) Synthesis of Organic Semiconductor Material 6

Using a 50 mL round bottomed flask, 186 mg of 4-trifluoromethylphenylacetonitrile (1.0 mmol) and 100 mg of biphenyl-2,2'-dicarboxaldehyde (0.5 mmol) were dissolved in 5 mL of ethanol and 15 mL of THF with stirring under nitrogen atmosphere. To the solution, an ethanol solution (2 mL) of 11 mg of potassium t-butoxide (0.1 mmol) was added dropwise at 0° C. with magnetic stirring. After the mixture was stirred for an additional 2 hours at room temperature, methanol was added. The resulting crystal was collected by suction filtration. The crystal was thoroughly washed with methanol and dried under reduced pressure in a desiccator to give a crude product. The crude product was recrystallized from chloroform to give an organic semiconductor material 6:

(2Z,2'Z)-3,3'-(4,4'-biphenyl)bis(2-(4-trifluoromethyl)phenylacrylonitrile) (abbrev.: $CF_3CN$-DSBP, compound (A2), pale blue crystal). Yield: 230 mg (90%).

(2) Fabrication of Organic Thin-Film Transistor 6

An organic thin film transistor 6 according to Example 6 having the structure as shown in FIG. 1 was obtained according to the procedure similar to that of Example 1 except that the organic semiconductor material 6 was used instead of the organic semiconductor material 1.

Example 7

(1) Synthesis of Organic Semiconductor Material 7

Using a 100 mL round bottomed flask, 170.1 mg of difluoroaldehyde (1.0 mmol) and 370.3 mg of 4-trifluoromethylphenylacetonitrile (2.0 mmol), were dissolved in ethanol (49 mL) under nitrogen atmosphere. To the solution, an ethanol solution (1 mL) of 6.8 mg of sodium ethoxide (2.0 mmol) was added dropwise at room temperature with magnetic stirring. After the mixture was stirred for an additional 1 hour and cooled to 0° C., methanol was added. The resulting crystal was collected by suction filtration. The crystal was thoroughly washed with methanol and dried under reduced pressure in a desiccator to give 469.1 mg of crude product of difluorinated distyryl derivative (ca. 93%). The crude product was recrystallized from hexane/chloroform to give (2Z,2'Z)-3,3'-(2,5-difluoro)bis(2-(4-trifluoromethyl)phenylacrylonitrile) (abbrev.: $CF_3CN$-DSBF$_2$, compound (E6), yellow crystal). Yield: 395.7 mg (78%).

(2) Fabrication of Organic Thin-Film Transistor 7

An organic thin film transistor 7 according to Example 7 having the structure as shown in FIG. 1 was obtained according to the procedure similar to that of Example 1 except that the organic semiconductor material 7 was used instead of the organic semiconductor material 1.

Comparative Example 1

(1) Synthesis of Organic Semiconductor Material 8

An organic semiconductor material 8:
(2Z,2'Z)-3,3'-(1,4-phenylene)bis(2-(4-methyl)phenylacrylonitrile) (abbrev.: $CH_3CN$-DSB) was synthesized according to the procedure similar to that of Example 1 except that the 4-methylphenylacetonitrile was used instead of 4-trifluoromethylphenylacetonitrile.

(2) Fabrication of Organic Thin-Film Transistor 8

An organic thin film transistor 8 according to Comparative example 1 having the structure as shown in FIG. 1 was obtained according to the procedure similar to that of Example 1 except that the organic semiconductor material 8 was used instead of the organic semiconductor material 1.

Comparative Example 2

(1) Synthesis of Organic Semiconductor Material 9

An organic semiconductor material 9:
(2Z,2'Z)-3,3'-(1,4-phenylene)bis(2-(4-fluoro)phenylacrylonitrile) (abbrev.: FCN-DSB) was synthesized according to the procedure similar to that of Example 1 except that the 4-fluorophenylacetonitrile was used instead of 4-trifluoromethylphenylacetonitrile.

(2) Fabrication of Organic Thin-Film Transistor 9

An organic thin film transistor 9 according to Comparative example 2 having the structure as shown in FIG. 1 was obtained according to the procedure similar to that of Example 1 except that the organic semiconductor material 9 was used instead of the organic semiconductor material 1.

Characterization

Characterization of output characteristics and transfer characteristics of organic thin-film transistors 1-9 fabricated under vacuum ($10^{-5}$ torr or less) was carried out using Keithley Model 2612A Dual-Channel System SourceMeter® by applying a voltage of −100 V between the source—and drain electrodes of each organic thin-film transistor and varying the gate voltage from −100 V to 100 V.

Figure 3:
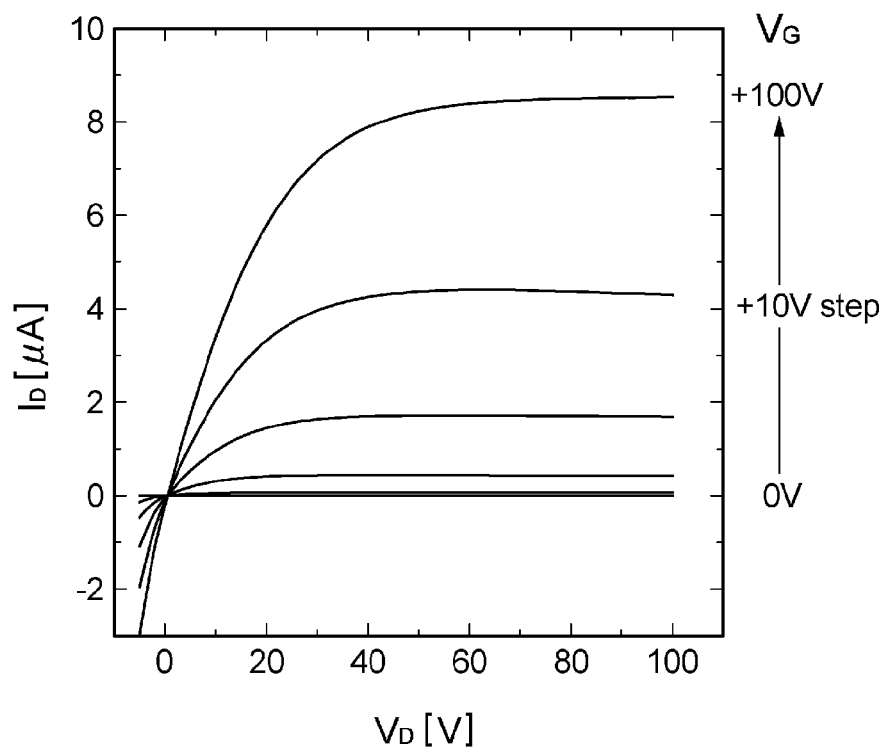
FIG. 3 shows output characteristics of the organic thin-film transistor 2.
Figure 4:
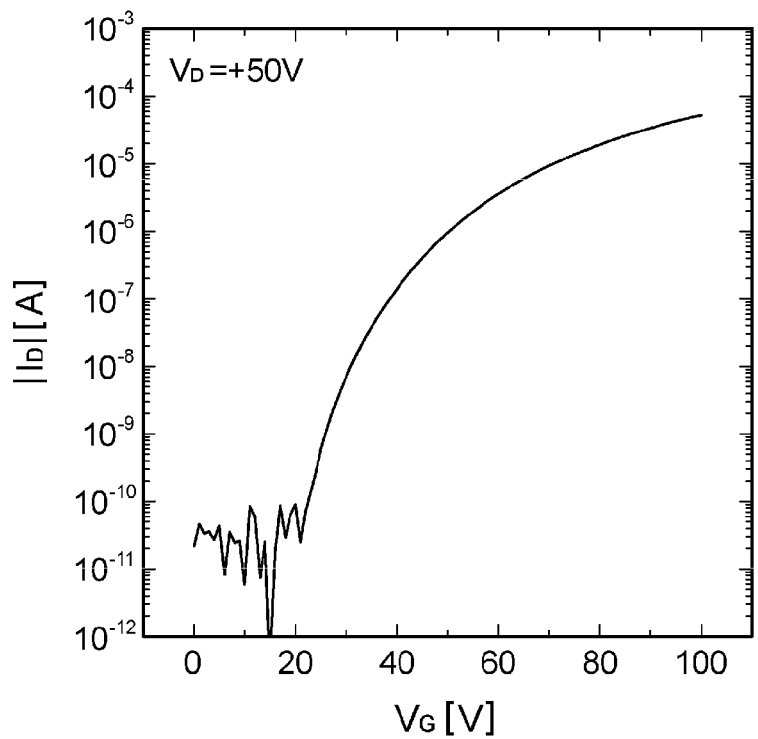
FIG. 4 shows transfer characteristics of the organic thin-film transistor 2.

As a representative example, the output characteristics and the transfer characteristics of organic thin-film transistor 2 (Example 2) are shown in FIG. 3 and FIG. 4, respectively.

The ratio of maximum current value and minimum current value observed in the characterization of the transfer characteristic was defined as the ON/OFF ratio of each organic thin-film transistor. The carrier mobility of each organic thin-film transistor was estimated from the saturated region of the transfer characteristic. The ON/OFF ratio and the carrier mobility of the organic thin-film transistor are shown in Table 1.

TABLE 1

| | organic thin-film transistor | organic semiconductor material | ON/OFF ratio | carrier mobility [$cm^2$/V · sec] | polarity |
|---|---|---|---|---|---|
| Example 1 | organic thin-film transistor 1 | $CF_3CN$-DSB | $10^6$ | 0.13 | n |
| Example 2 | organic thin-film transistor 2 | $CF_3CN$-DS2T | $10^6$ | 0.08 | n |
| Example 3 | organic thin-film transistor 3 | $CF_3CN$-DSTT | $10^6$ | 0.05 | n |
| Example 4 | organic thin-film transistor 4 | $C_6F_{13}CN$-DSB | $10^3$ | 0.001 | n |
| Example 5 | organic thin-film transistor 5 | $CF_3CN$-DS1T | $10^6$ | 0.03 | n |
| Example 6 | organic thin-film transistor 6 | $CF_3CN$-DSBP | $10^4$ | 0.001 | n |
| Example 7 | organic thin-film transistor 7 | $CF_3CN$-DSBF$_2$ | $10^6$ | 0.13 | n |
| Comparative example 1 | organic thin-film transistor 8 | $CH_3CN$-DSB | — | — | — |
| Comparative example 2 | organic thin-film transistor 9 | FCN-DSB | — | — | — |

Example 8

(1) Synthesis of Organic Semiconductor Material 1

The organic semiconductor material 1:
(2Z,2'Z)-3,3'-(1,4-phenylene)bis(2-(4-trifluoromethyl)phenylacrylonitrile) (abbrev.: $CF_3CN$-DSB, compound (A1)) was synthesized according to the procedure similar to that of Example 1.

(2) Fabrication of Organic Thin-Film Transistor 10

Figure 5:
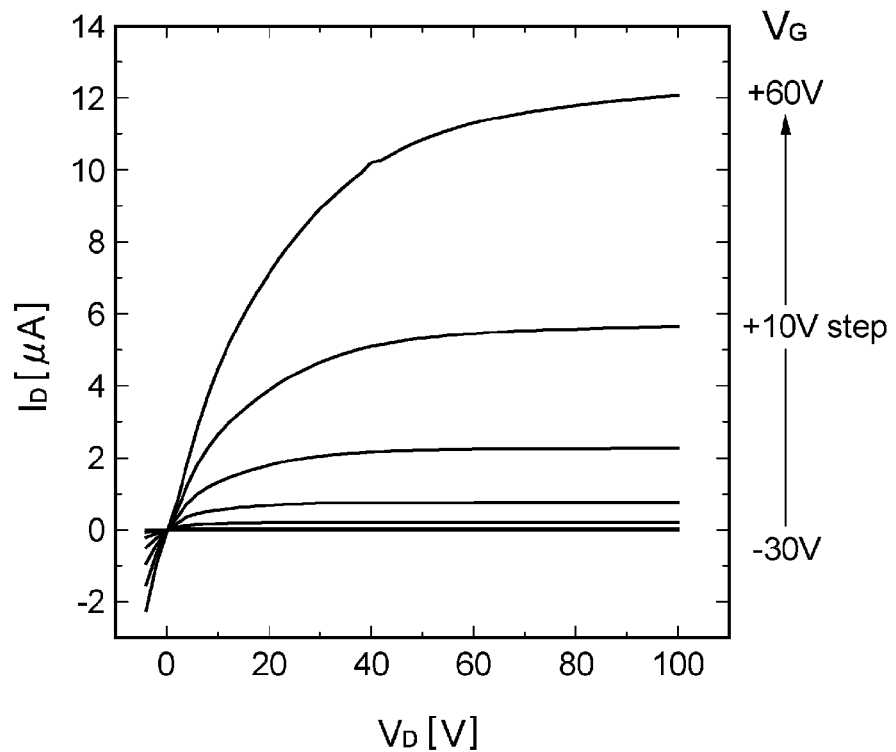
FIG. 5 shows output characteristics of the organic thin-film transistor 10.
Figure 6:
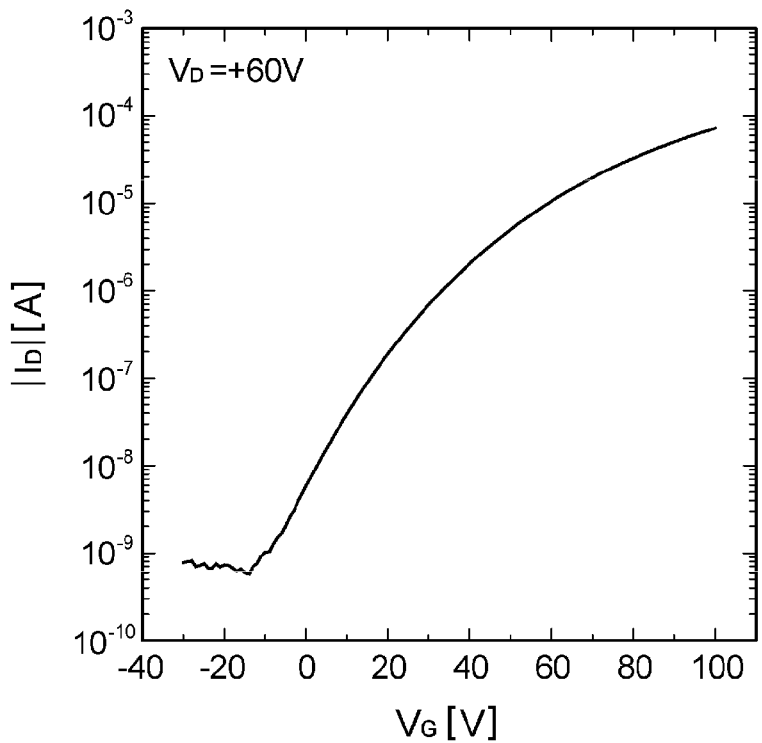
FIG. 6 shows transfer characteristics of the organic thin-film transistor 10.

As a substrate, a PEN film (thickness: 100 μm) was used instead of a silicon wafer with thermal oxidized film, on which a gate electrode was formed by vacuum deposition of Au (40 nm)/Ti (5 nm). As a gate insulator film, an insulator film of polyimide (capacitance: C=4.5 nF/$cm^2$) having the thickness of ca. 600 nm was formed by spin-coating of a precursor solution of the polyimide followed by heat treatment. An organic thin film transistor 10 according to Example 8 having the structure as shown in FIG. 2 was fabricated by depositing the organic semiconductor layer 1 having the thickness of ca. 30 nm on top of the polyimide insulator film under vacuum, follow by depositing Au (thickness: 40 nm, L=20 μm, W=2 mm) as the source and the drain electrodes. The output characteristics and the transfer characteristics of organic thin-film transistor 10 are shown in FIG. 5 and FIG. 6, respectively. The ON/OFF ratio and the carrier (electron) mobility of the organic thin-film transistor 10 estimated similarly to the aforementioned Examples were $10^5$ and 0.1 [$cm^2$/V·sec], respectively.

Example 9

(1) Synthesis of Organic Semiconductor Material 1

The organic semiconductor material 1:
(2Z,2'Z)-3,3'-(1,4-phenylene)bis(2-(4-trifluoromethyl)phenylacrylonitrile) (abbrev.: $CF_3CN$-DSB, compound (A1)) was synthesized according to the procedure similar to that of Example 1.

(2) Fabrication of Organic Thin-Film Transistor 11

A silicon wafer with 300 nm of thermally oxidized silicon dioxide film (SUMCO CORPORATION, 1×1 cm (area: 1 $cm^2$), thickness: 525 µm) was used as a gate electrode and a gate insulator layer. A organic semiconductor layer was formed by drop casting of the solution of the organic semiconductor material 1 having the concentration of 1 mg/mL to the surface of the oxidized film.

A source electrode and a drain electrode of Au having the thickness of ca. 30 nm was formed by vacuum deposition using shadow masks, by which an organic thin film transistor 11 according to Example 9 having the structure as shown in FIG. 1 was fabricated. Channel length (L) and channel width (W) of the source and the drain electrodes are 20 µm and 2 mm, respectively. The ON/OFF ratio and the carrier (electron) mobility of the organic thin-film transistor 11 estimated similarly to the aforementioned Examples were $10^3$ and 0.0002 [$cm^2$/V·sec], respectively.

Example 10

(1) Synthesis of Organic Semiconductor Material 1

The organic semiconductor material 1:
(2Z,2'Z)-3,3'-(1,4-phenylene)bis(2-(4-trifluoromethyl)phenylacrylonitrile) (abbrev.: $CF_3CN$-DSB, compound (A1)) was synthesized according to the procedure similar to that of Example 1.

(2) Fabrication of Organic Thin-Film Transistor 12

An organic thin film transistor 12 was obtained according to the procedure similar to that of Example 1 except that the Ag was used instead of Au as the source and the drain electrodes. The source and the drain electrodes were formed by the vacuum deposition process, of which thickness is ca. 30 nm.

The ON/OFF ratio and the carrier (electron) mobility of the organic thin-film transistor 12 estimated similarly to the aforementioned Examples were $10^6$ and 0.20 [$cm^2$/V·sec], respectively.

Examples 11-13

The organic thin film transistor 1 was fabricated according to the procedure similar to that of Example 1 and its atmospheric operation test, atmospheric exposure stability test and characterization of crystallinity were carried out.

Example 11

Atmospheric operation test (Tests 1-4) of the organic thin-film transistor 1 as followings were carried out. The characterizations were carried out similarly to those of Example 1 and the like. Characterization of transfer characteristics of organic thin-film transistor 1 was carried out using Keithley Model 2612A Dual-Channel System SourceMeter® by applying a voltage of −100 V between the source- and drain electrodes of each organic thin-film transistor and varying the gate voltage from −100 V to 100 V. The carrier mobility was estimated from the saturated region of the transfer characteristic.

Deterioration rate of the mobility was estimated using the mobility obtained in Test 1 as an initial value. Shift in threshold was estimated from the shift amount from the value estimated in Test 1.

Test 1: The characterization of the organic thin-film transistor 1 just after fabrication was carried out under vacuum ($10^{-5}$ torr or less).

Test 2: The organic thin-film transistor 1 was exposed to the atmosphere after Test 1, then the characterization was carried out immediately in the atmosphere.

Test 3: The organic thin-film transistor 1 was exposed to the atmosphere after Test 2, which was subjected to the characterization every few hours in the atmosphere. The organic thin-film transistor 1 was stored in the dark atmosphere.

Test 4: The characterization of the organic thin-film transistor 1 after Test 3 under vacuum ($10^{-5}$ torr or less).

Figure 7:
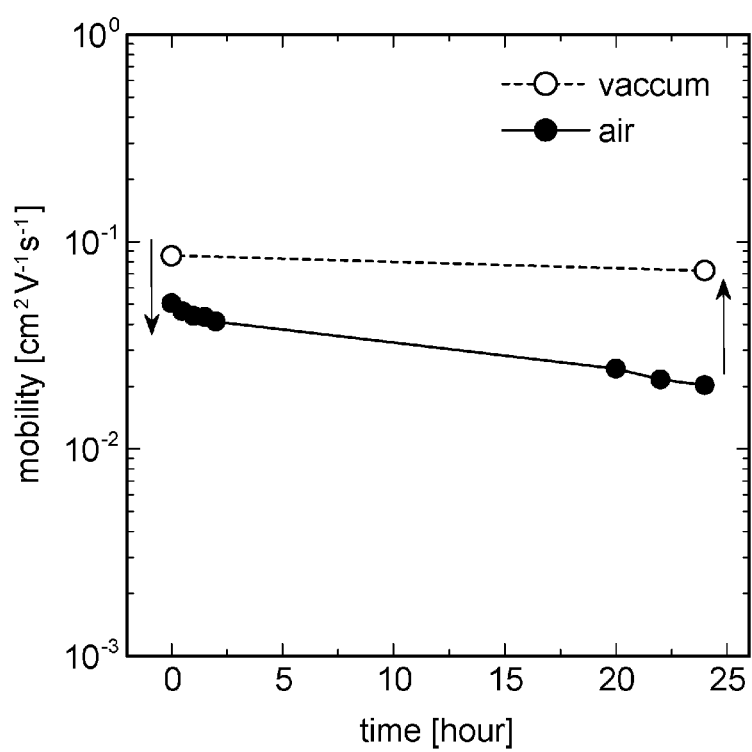
FIG. 7 shows mobility of the organic thin-film transistor 1 calculated from the result of atmospheric operation test.

Results are shown in Table 2 and FIG. 7.

It is clear from Table 2 and FIG. 7 that the organic thin-film transistor 1 may be operated in the atmosphere since it shows n-type characteristic. In addition, the result of the characterization of the organic thin-film transistor 1 under vacuum ($10^{-5}$ ton or less) carried out after 24 hours of operation in the atmosphere showed recovery of characteristics deteriorated in the atmosphere.

TABLE 2

| | mobility µ[$cm^2$/V · s] | deterioration rate Δµ[%] | shift in threshold $\Delta V_{th}$[V] |
|---|---|---|---|
| Test 1 | 0.085 | — | — |
| Test 2 | 0.050 | 41 | — |
| Test 3 | 0.020 | 76 | — |
| Test 4 | 0.073 | 14 | 7 |

Example 12

Atmospheric exposure stability test of the organic thin-film transistor 1 was carried out. The organic thin-film transistor 1 was stored in dark atmosphere for a certain period of time, which was subjected to the characterization under vacuum ($10^{-5}$ torr or less). The characterization was carried out according to the procedure as in Example 11. Results are shown in FIG. 8.

Figure 8:
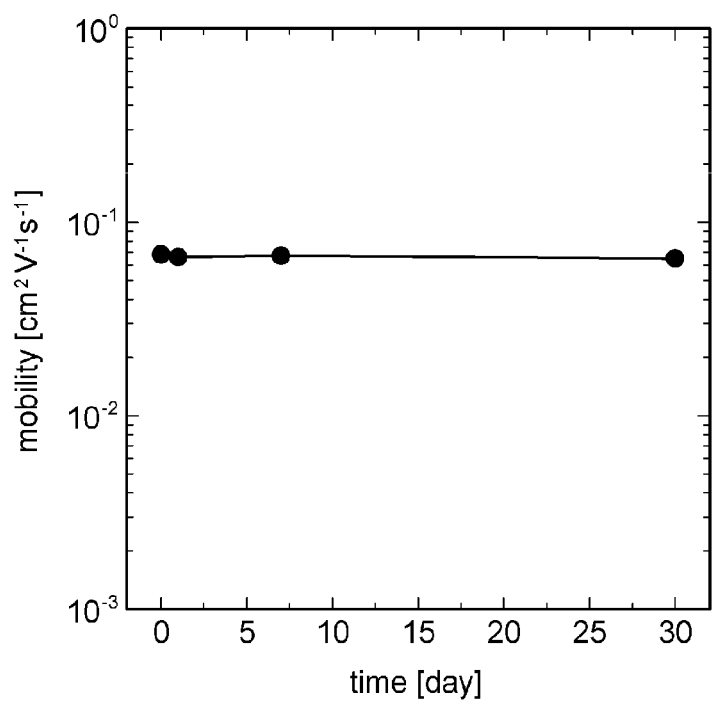
FIG. 8 shows the result of atmospheric exposure stability test of the organic thin-film transistor 1.

It is seen from FIG. 8 that no significant deterioration in the characteristics is not observed after 30 days of atmospheric exposure.

Example 13

The crystallinity of the organic semiconductor layer in the organic thin-film transistor 1 was characterized as follows.

Figure 9:
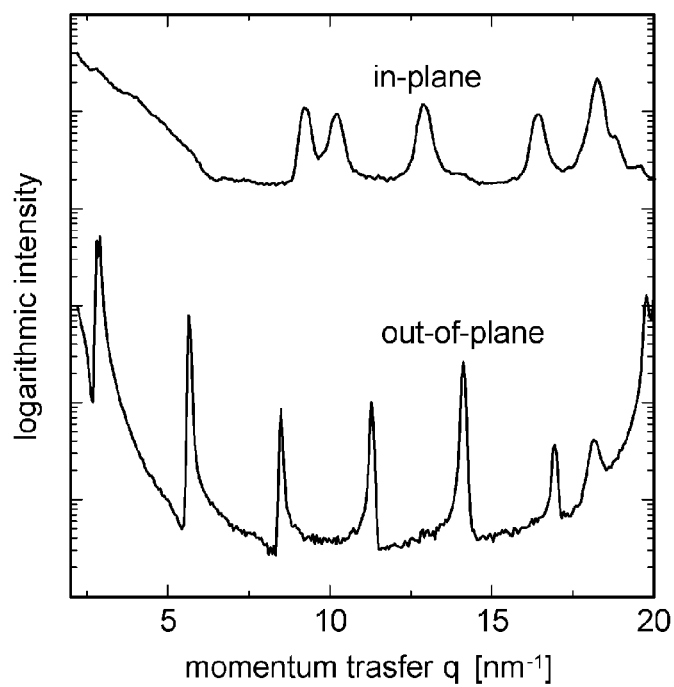
FIG. 9 shows thin-film X-ray diffraction pattern of the organic thin-film transistor 1.

The characterization of the crystallinity was carried out by measuring in-plane and out-of-plane X-ray diffraction (XRD) of the organic semiconductor layer using ATX-GSOR for structure characterization of thin film in BL46XU beamline of synchrotron radiation facility SPring-8. Results are shown in FIG. 9.

Diffraction peaks in each in-plane and out-of-plane XRD profile show that the organic semiconductor layer in the organic thin-film transistor 1 is crystalline thin film. Moreover, fifth and higher order peaks observed in the out-of-plane diffraction profile show that the organic semiconductor layer is highly crystalline.

Example 14

The organic thin film transistor 7 was fabricated according to the procedure similar to that of Example 7 and its atmospheric operation tests were carried out as follows:

Test 1: The characterization of the organic thin-film transistor 7 just after fabrication was carried out under vacuum ($10^{-5}$ torr or less).

Test 2: The organic thin-film transistor 7 was exposed to the atmosphere after Test 1, then the characterization was carried out immediately in the atmosphere.

Test 3: The organic thin-film transistor 7 was exposed to the atmosphere after Test 2, stored in the atmosphere for 24 hours, which was subjected to the characterization in the atmosphere. The organic thin-film transistor 1 was stored in the dark atmosphere.

Figure 10:
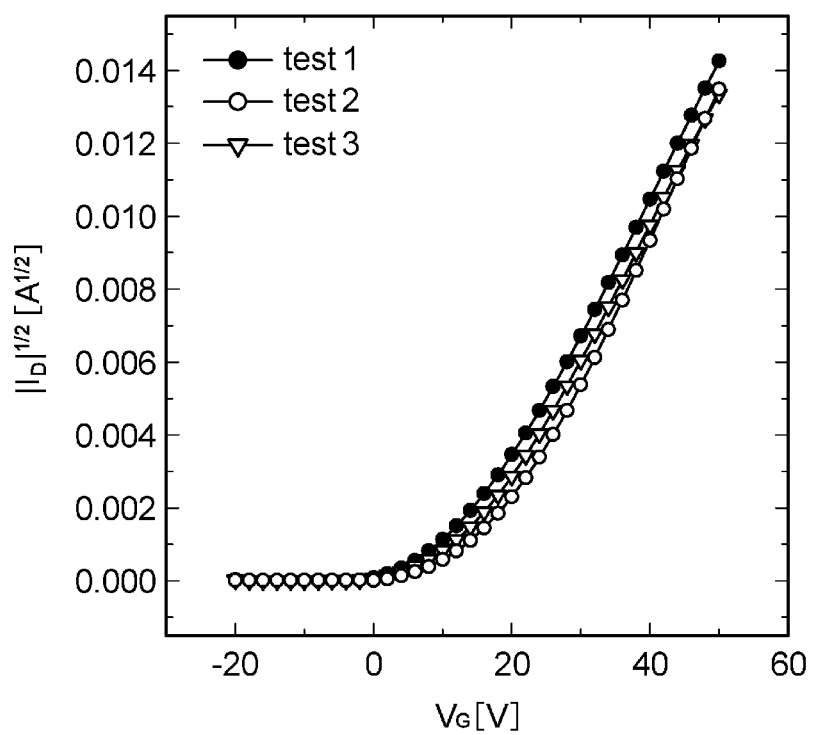
FIG. 10 shows the result of atmospheric operation test of the organic thin-film transistor 7.

Results are shown in FIG. 10.

It is clear from FIG. 10 that the organic thin-film transistor 7 may be operated in the atmosphere since it shows n-type characteristic in the atmosphere. In addition, the result of the characterization of the organic thin-film transistor 1 in the atmosphere carried out after 24 hours of operation in the atmosphere (Test 3) showed the deterioration of ca. 10% from initial state (Test 1), by which it was confirmed that the organic semiconductor material was very stable in the atmosphere.

INDUSTRIAL APPLICABILITY

The organic semiconductor material of the present invention is preferably applicable to the organic semiconductor layer for the organic thin-film-transistor because of its high carrier mobility and chemical stability. Also, the production cost of the organic semiconductor material of the present invention may be reduced since its film may be formed at relatively low temperature as well as using by a simple production process such as a coating process.

The organic thin-film transistor in which the organic semiconductor material is used may be applied to various integrated circuits (IC) because of its large ON/OFF ratio and high response rate. Also, the organic semiconductor material of the present invention may be widely applied to light emitting materials and charge injection materials for organic EL devices, charge conductive materials and organic laser oscillators because of its excellent electronic properties.

INDICATION BY REFERENCES NUMERALS

1: substrate
2: gate electrode
3: gate insulator layer
4: organic semiconductor layer
5: source electrode
6: drain electrode
10: organic thin-film transistor

The invention claimed is:
1. An organic thin-film transistor comprising a gate electrode, a gate insulator layer, an organic semiconductor layer, a source electrode and a drain electrode, wherein the organic semiconductor layer comprises an organic semiconductor material having the structure represented by formula (E6) shown below, and the organic semiconductor layer has crystallinity:

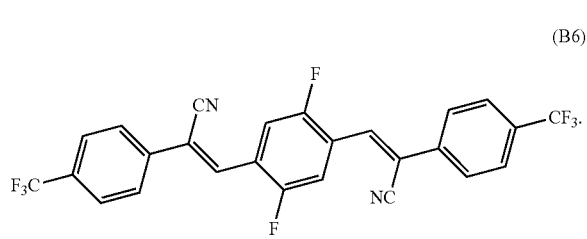 [SMILES: N#C/C(=C\c1cc(F)c(/C=C(\C#N)c2ccc(C(F)(F)F)cc2)cc1F)c1ccc(C(F)(F)F)cc1]

(B6)

* * * * *